(12) United States Patent
Klein

(10) Patent No.: US 7,664,225 B2
(45) Date of Patent: Feb. 16, 2010

(54) PROCESS AND DEVICE FOR THE FAST OR ON-LINE DETERMINATION OF THE COMPONENTS OF A TWO-COMPONENT OR MULTI-COMPONENT SYSTEM

(75) Inventor: Albert Klein, Simmersfeld (DE)

(73) Assignee: Elisabeth Katz, Simmersfeld (DE)

( * ) Notice: Subject to any disclaimer, the term of this patent is extended or adjusted under 35 U.S.C. 154(b) by 0 days.

(21) Appl. No.: 12/088,749

(22) PCT Filed: Sep. 28, 2006

(86) PCT No.: PCT/EP2006/009413

§ 371 (c)(1),
(2), (4) Date: Jul. 10, 2008

(87) PCT Pub. No.: WO2007/036359

PCT Pub. Date: Apr. 5, 2007

(65) Prior Publication Data

US 2008/0285714 A1    Nov. 20, 2008

(30) Foreign Application Priority Data

Sep. 29, 2005    (DE) .................. 10 2005 046 878

(51) Int. Cl.
*G01N 23/223* (2006.01)
*G01N 23/20* (2006.01)

(52) U.S. Cl. .......................... 378/45; 378/70
(58) Field of Classification Search ............. 378/44–47, 378/70, 90
See application file for complete search history.

(56) References Cited

U.S. PATENT DOCUMENTS

| 3,404,275 A | 10/1968 | Martinelli |
| 3,567,929 A | 3/1971 | White et al. |
| 3,710,104 A | 1/1973 | Pavlik |
| 3,944,822 A | 3/1976 | Dzubay |
| 4,486,894 A | 12/1984 | Page et al. |

(Continued)

FOREIGN PATENT DOCUMENTS

EP    0 380 226 A1    8/1990

OTHER PUBLICATIONS

"An axially symmetrical gamma-ray backscatter system for DuMond spectrometry," Innes K. MacKenzie; Department of Physics, University of Guelph, Guelph, Ontario, Canada N1G 2W1; Nuclear Instruments and Methods in Physics Research A299 (1990) 377-381, North-Holland.

(Continued)

*Primary Examiner*—Irakli Kiknadze
(74) *Attorney, Agent, or Firm*—Rabin & Berdo, PC

(57) ABSTRACT

Process and device for fast or on-line determination of the components of a two-component or multiple-component system in which the elements which constitute the individual components differ by their atomic number. The following steps are carried out: the surface of the substance is irradiated with polychromatic X-ray or monochromatic gamma radiation, the X-ray radiation exhibiting in the energy range from 1 to 30 keV one or more peaks in the continuum. The spectrum of the radiation backscattered and emitted by the substance is measured in an energy range from 1 to 30 keV with a resolution of at least 250 eV. The spectrum is analysed in that at least the intensities of the elastically backscattered and inelastically backscattered peaks are separately determined and at least some $K_a$ or $L_a$ fluorescence peaks in the energy range from 1 to 30 keV are used in order to compensate for the influence of a fluctuating elemental composition within a component.

12 Claims, 3 Drawing Sheets

U.S. PATENT DOCUMENTS

| | | | | |
|---|---|---|---|---|
| 6,130,931 | A | * | 10/2000 | Laurila et al. ............... 378/45 |
| 6,496,562 | B1 | * | 12/2002 | Henrich et al. ............... 378/90 |
| 2002/0097833 | A1 | * | 7/2002 | Kaiser et al. ............... 378/45 |
| 2004/0240606 | A1 | * | 12/2004 | Laurila et al. ............... 378/45 |

OTHER PUBLICATIONS

"Analysis of Metal Alloys by Rayleigh to Compton Ratios and X-ray Fluorescence Peaks In The 50 to 122 keV Energy Range," 1) G. E. Gigante; Dipartimento di Scienze Biomediche, Universita dell Aquila, 67100 L'Aquila, Italy 2) L. J. Pedraza; International Centre for Theoretical Physics, P.O. Box 586, 34100 Trieste, Italy and 3) S. Sciuti; Dipartimento di Energetico, Universita di Roma "La Sapienza," 00100 Roma, Italy; received Feb. 20, 1985 and in revised form Apr. 11, 1985; Nuclear Instruments and Methods in Physics Research B12 (1985) 229-234, North-Holland, Amsterdam.

* cited by examiner

PROCESS AND DEVICE FOR THE FAST OR ON-LINE DETERMINATION OF THE COMPONENTS OF A TWO-COMPONENT OR MULTI-COMPONENT SYSTEM

TECHNICAL FIELD OF THE INVENTION

The invention relates to a device for the fast or online determination of the components of a two-component or multi-component system as defined in the preamble to claim 1, as well as to a process as disclosed in claim 3.

In the mining and steel industry, the problem frequently arises that the ash content of coal, coke, or the like must be determined continuously (online) or at short intervals. Radiometric methods are frequently used to determine this ash content, in particular for the online measurements. The most widely used measuring method is the so-called dual-energy method, for which the goods to be measured is irradiated with X-ray radiation or gamma radiation having different energy. A $Cs^{137}$ source with a photon energy of 600 keV and an $Am^{241}$ source with a photon energy of approximately 60 keV are used in most cases. The weakening of the two types of radiation while passing through the substance is then measured and a conclusion drawn as to the mean density and the mean atomic number. The ash content can be computed from the obtained information if the composition of the ash is constant.

PRIOR ART

A device and a process for determining the ash content of coal is known from the reference GB 89 13 238.6, which discloses measuring the radiation emitted by the $Am^{241}$ source and is backscattered by the sample, in addition to using the above-mentioned dual-energy method. Used for this is a radiation detector with a high enough resolution to distinguish between the elastically backscattered component (Rayleigh scattering) and the inelastic component of the scattering (Compton scattering). As a result of the Z-dependence of the Compton scattering, it is possible to draw conclusions concerning the ash content from the ratio of Compton peak to Rayleigh peak, so that the precision of the dual-energy method can be improved.

The disadvantage of the device proposed in this reference is the necessary high apparatus expenditure, as well as—in particular because of the $Cs^{137}$ source—the necessary radiation protection measures, wherein furthermore only 2 different methods are used for determining the mean atomic number, which limits the increase in information.

SUBJECT—MATTER OF THE INVENTION

Starting with this premise, it is the object of the present invention to develop a device and a process for the automatic fast determination or the online determination of the components of a two-component or a multi-component system, which on the one hand uses only a small number of radiation sources and radiation detectors and, on the other hand, has low requirements with respect to radiation protection.

This object is solved with a device having the features as disclosed in claim 1 and with a process having the features as disclosed in claim 3.

For the process according to the invention and the device according to the invention, an X-ray tube that is operated with relatively low acceleration voltage or a low-energy gamma radiator, e.g. a Fe-55, is used and the backscattered or emitted spectrum for the substance is then measured in back-scattering direction with the aid of a high-resolution radiation detector. The energy range for the spectrum in this case is selected such that the observed interval contains $K_\alpha$ lines and/or $K_\beta$ lines of the elements of interest—in particular aluminum, silicon, phosphorus, sulfur, potassium, calcium, titanium, manganese, cobalt and iron—as well as a Rayleigh peak and the associated Compton peak of the anode material for the X-ray tube or the gamma radiator. The $K_\alpha$ lines of the above-listed elements are in the energy range between 1 and 7 keV, so that an acceleration voltage between 10 and 50 kV, preferably between 10 and 20 kV, is suitable. Copper is particularly suitable as anode material since the $K_\alpha$ line of copper has an energy of approximately 8 keV, meaning it directly follows the $K_\alpha$ energy window ranging from aluminum to nickel.

In order to determine the components of the substance, the intensities of the Compton peak and the Rayleigh peak for the incident X ray radiation are determined along with the intensities of all or individual fluorescence emission peaks of the substance. The preferably used ratio of Compton peak to Rayleigh peak is comparatively independent of interference variables since the two lines have almost identical energy and are therefore influenced in the same way by interference variables, such as the photoelectric effect, thus permitting a direct conclusion as to the mean atomic number for the substance. An extremely precise and fast analysis is therefore possible with further knowledge of the qualitative spectrum or, following a respective calibration, of the quantitative fluorescence spectrum. The spectrum is particularly suitable for determining the ash content of coal.

The special advantage of this process is that a single radiation source and a single radiation detector are sufficient and that the radiation source can be an X-ray tube with relatively low acceleration voltage.

The invention is explained in the following with the aid of an exemplary embodiment, showing in:

DETAILED DESCRIPTION OF THE PREFERRED EMBODIMENT

Figure 1:
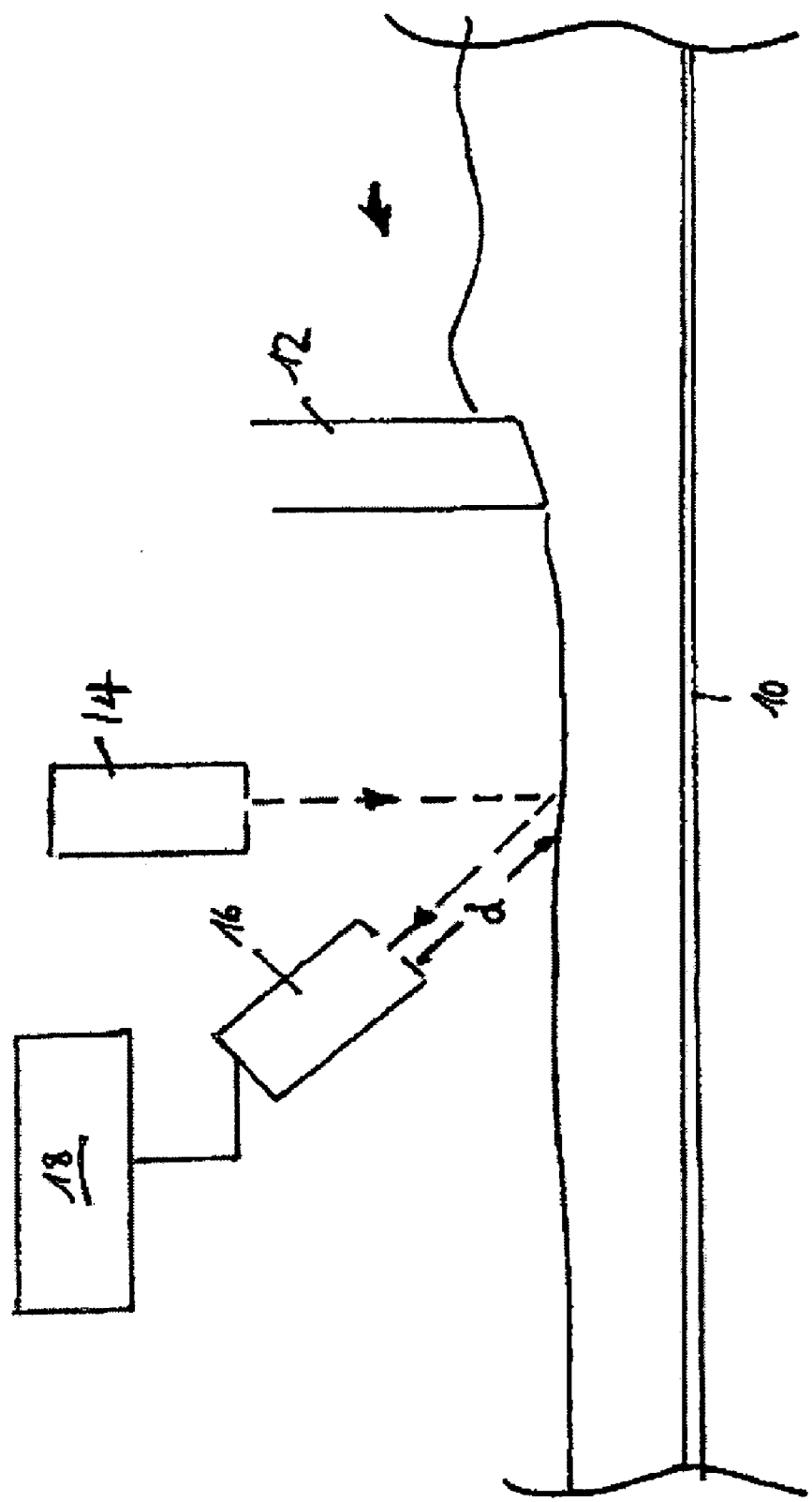
FIG. 1 A schematic representation of a device for the online measuring of the ash content of coal.

FIG. 1 schematically shows a device for the online determination of the ash content of a coal stream K that is conveyed on a conveying belt 10.

Initially, the surface of the coal stream K is leveled with the aid of the leveling plough 12, wherein surface fluctuations still occur even after the leveling operation because of the grain size. The measuring device consists of the X-ray tube 14, arranged above the conveyor belt 10, the radiation detector 16 that is also arranged above the conveyor belt 10, and the evaluation unit 18 connected to the detector.

For the following example, the X-ray tube 14 is operated with an acceleration voltage of between 10 and 20 kV and comprises a copper anode. The direction of irradiation is perpendicular to the surface of the conveyor belt 10. The axis of the radiation detector 16 is positioned at an angle of approximately 45° to the irradiation direction of the X-ray tube 14, wherein the distance d between the radiation detector and the surface of the coal stream K is preferably approximately 10 cm. The radiation detector 16 is a silicon drift detector with a resolution of approximately 160 eV. The radiation detector 16 and the evaluation unit 18 detect and evaluate an X ray spectrum ranging from 1 to 10 keV.

Figure 2:
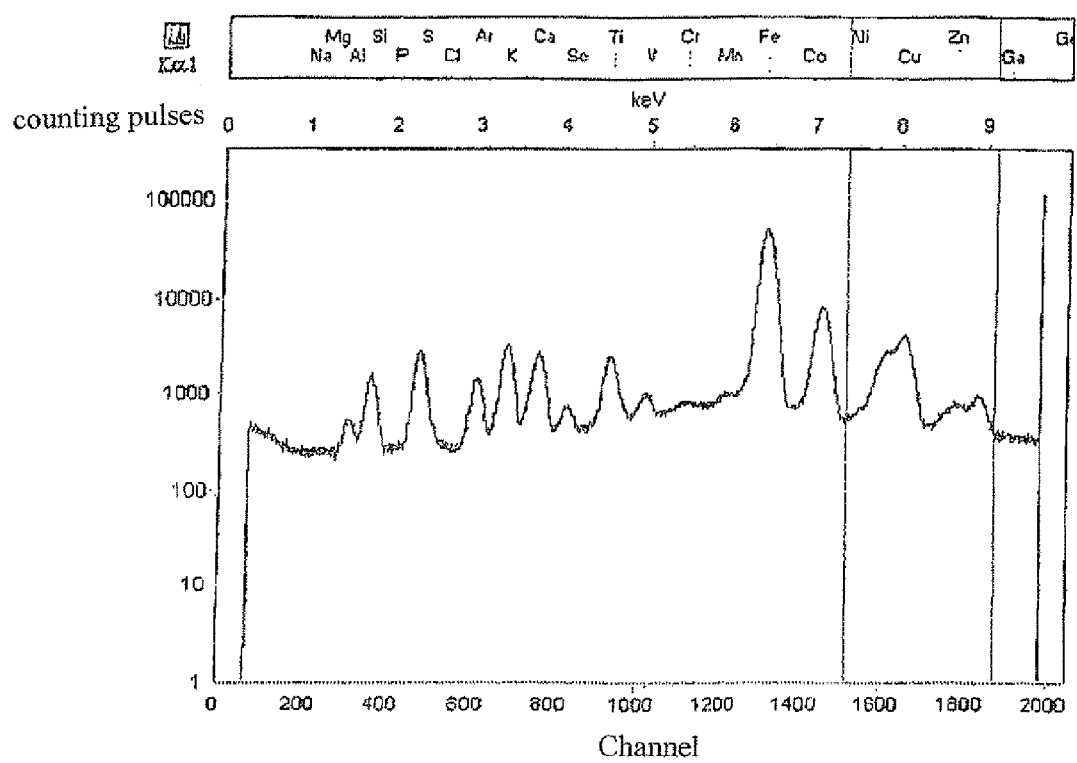
FIG. 2 A typical spectrum displayed on the radiation detector in FIG. 1.
Figure 3:
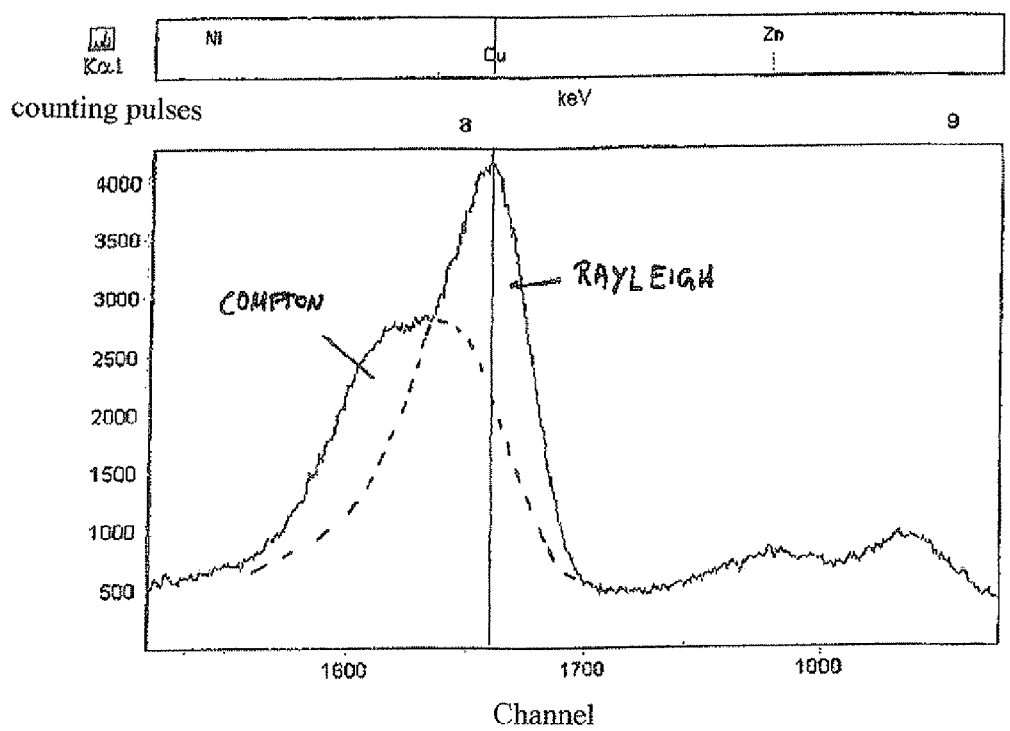
FIG. 3 A segment of the spectrum shown in FIG. 2.

FIG. 2 shows a typical spectrum, such as is recorded by the radiation detector 16. FIG. 3 shows a detail thereof, in the range of approximately 7.5 to 9 keV. It is possible to see aluminum, silicon, sulfur, argon (a component of the ambient air), potassium, calcium, selenium, titanium, vanadium, iron and cobalt in addition to the $K_\alpha$ peaks of various elements. Also visible is the $K_\alpha$ line of copper, which however does not result from the copper element in the conveyed coal, but represents the backscattered signal of the copper anode. When viewing FIG. 3, we can see that with a suitable resolution, the Rayleigh component of the copper peak can be separated from the Compton component. The ratio of these two components depends on the mean atomic number of the backscattering material, which in this case is the coal stream K; see for example the reference document DE-OS 2920364.

If we know the precise composition of the coal ash (the ash formers all have a higher Z than carbon), then the ash content can be determined solely from the ratio of Rayleigh component to Compton component. However, the composition of the ash fluctuates so that the low-energy portion of the spectrum is additionally considered, which contains the $K_\alpha$ lines of the essential ash formers. If the air absorption no longer plays a dominant role—as is the case for distance fluctuations below 20% and a photon energy above 2 keV—the ash composition can be determined directly from the intensity ratio of the $K_\alpha$ peaks. Thus, an absolute measurement is not required in this case, which would be difficult to obtain because of the fluctuating distance between the sample surface and the radiation detector and the $1/r^2$ dependence of the radiation intensity. Nevertheless, we can obtain an absolute measurement of the ash content with the following steps, which are of course automated:

The ash composition is known from the ratio of the $K_\alpha$ peaks in the energy range below 7.5 keV because the $K_\alpha$ lines of the essential ash formers are located in this energy range. From this—and if necessary using calibration spectra—it is possible to determine the mean atomic number for the ash. By analyzing the backscattered copper $K_\alpha$ line, meaning by determining the ratio of the Compton backscattering to the Rayleigh backscattering, we can obtain the mean atomic number for the sample. Since the mean atomic number of coal is known, of course, it is possible to obtain the absolute ash content from this information as well. A distance compensation or a time averaging should be carried out, if necessary, in cases where the lighter elements are extremely important, in particular aluminum and silicon.

In practical operations, a product-specific and device-specific calibration is carried out to achieve the best possible accuracy, using formulas containing the Compton scattering as well as the Rayleigh scattering, along with the most important intensities of the fluorescence lines.

It is particularly advantageous if only one spectrum is needed, which is measured by a single radiation detector. As a result, it is always ensured that both types of information, namely the $K_\alpha$ emission and the scattering, come from the same geometric location on the sample and are always correlated.

The measured spectrum is evaluated automatically in the evaluation unit 18, in which corresponding reference spectra or comparison spectra are stored as a rule.

For this example, the device and the process were explained by using the online determination of the ash content of a coal stream. However, other applications are possible as well, for example the offline determination of the ash content of coal, for which the coal sample can be present in the form of a compressed pellet, following a corresponding sample preparation. The method used for the online determination of the ash content can furthermore also be used for paper webs.

REFERENCE NUMBER LIST

10 conveyor belt
12 leveling plough
14 X-ray tube
16 radiation detector
18 evaluation unit

The invention claimed is:

1. A device for fast determination or online determination of components of a substance in a two-component or multi-component system, the components including elements of different atomic numbers, said device comprising:
   at least one radiation source and at least one radiation detector arranged in a backscattering path, and;
   at least one evaluation unit that is respectively connected to the radiation detector; wherein
   the radiation source is a gamma-radiation source with an energy of 10-30 keV or an X-ray tube, operating with an acceleration voltage between 10 kV and 50 kV, and including an anode of Cu, Mo, Rh or W;
   the radiation detector is sensitive in an energy range of 1 keV to 30 keV, and has a resolution of at least 250 eV; and
   the evaluation unit analyzes a spectrum of a radiation that is backscattered elastically or inelastically by the substance, and the emitted radiation in an energy range between 1 keV and 30 keV.

2. The device according to claim 1, characterized in that only one radiation detector is connected to the evaluation unit.

3. The device of claim 1, wherein the spectrum of the radiation is in an energy range between 1 keV and 10 keV.

4. The device of claim 3, wherein the spectrum of the radiation is in an energy range between 2 keV and 9 keV.

5. The device of claim 1, wherein the radiation detector has a resolution of at least 160 eV.

6. A process for fast determination or online determination of components of a substance in a two-component or multi-component system, the components including elements of different atomic numbers, said process comprising:
   irradiating a surface of the substance with polychromatic X-ray radiation or monochromatic gamma radiation, wherein the X-ray radiation exhibits one or several peaks in continuum in an energy range between 1 keV and 30 keV;
   measuring a spectrum of the radiation that is backscattered by the substance in an energy range between 1 keV and 30 keV, with a resolution of at least 250 eV;
   evaluating the spectrum, wherein at least intensities of elastically backscattered and inelastically backscattered peaks are determined separately, and at least several $K_\alpha$ or $L_\alpha$ fluorescence peaks in an energy range between 1 keV and 30 keV are used for compensating an influence of a fluctuating element composition within one of the components.

7. The process according to claim 6, wherein an ash content of coal are determined, which are conveyed on a moving conveyor.

8. The process according to claim 6, wherein an ash content of coal are determined, using a coal sample in the form of a compressed pellet.

9. The process according to claim 6, wherein an ash content of a paper web is determined.

10. The process of claim 6, wherein the spectrum of the radiation is in an energy range between 1 keV and 10 keV.

11. The process of claim 10, wherein the spectrum of the radiation is in an energy range between 2 keV and 9 keV.

12. The process of claim 6, wherein the spectrum of the radiation has a resolution of at least 160 eV.

* * * * *